(12) United States Patent
Seki et al.

(10) Patent No.: US 7,794,391 B2
(45) Date of Patent: Sep. 14, 2010

(54) ENDOSCOPE

(75) Inventors: Hidetoshi Seki, Saitama (JP); Kazuhiko Hino, Saitama (JP)

(73) Assignee: Fujinon Corporation, Saitama (JP)

( * ) Notice: Subject to any disclaimer, the term of this patent is extended or adjusted under 35 U.S.C. 154(b) by 788 days.

(21) Appl. No.: 11/043,409

(22) Filed: Jan. 27, 2005

(65) Prior Publication Data

US 2005/0203336 A1 Sep. 15, 2005

(30) Foreign Application Priority Data

Jan. 30, 2004 (JP) ............... 2004-023984

(51) Int. Cl.
*A61B 1/00* (2006.01)
*A61B 1/04* (2006.01)

(52) U.S. Cl. ...................... 600/139; 125/146

(58) Field of Classification Search ................ 600/125, 600/136, 139, 141, 144, 148, 132, 137, 146
See application file for complete search history.

(56) References Cited

U.S. PATENT DOCUMENTS

| | | | |
|---|---|---|---|
| 4,676,230 A | | 6/1987 | Miyazaki |
| 4,977,887 A | * | 12/1990 | Gouda ................ 600/144 |
| 5,002,042 A | * | 3/1991 | Okada ................ 600/127 |
| 5,359,992 A | * | 11/1994 | Hori et al. ................ 126/4 |
| 5,394,864 A | * | 3/1995 | Kobayashi et al. .......... 600/146 |
| 5,810,715 A | * | 9/1998 | Moriyama ................ 600/144 |
| 5,885,208 A | * | 3/1999 | Moriyama ................ 600/144 |
| 5,976,074 A | * | 11/1999 | Moriyama ................ 600/144 |
| 6,203,494 B1 | * | 3/2001 | Moriyama ................ 600/144 |
| 6,520,908 B1 | * | 2/2003 | Ikeda et al. ................ 600/132 |

FOREIGN PATENT DOCUMENTS

| | | |
|---|---|---|
| DE | 3603345 A1 | 8/1986 |
| JP | S59-41323 | 3/1984 |
| JP | 5-317237 A | 12/1993 |
| JP | 2000-152910 | 6/2000 |
| JP | 2002-253476 A | 9/2002 |

* cited by examiner

*Primary Examiner*—Linda C Dvorak
*Assistant Examiner*—Alireza Nia
(74) *Attorney, Agent, or Firm*—Rabin & Berdo, PC

(57) ABSTRACT

An endoscope capable of preventing the cover member from being damaged and also preventing the airtight failure from being caused is disclosed. A projection 172 can reparably join with an opening 137. It becomes possible for the cover fitting member 170 and the cover member 130 to rotate together as one body when they join with each other. When they enter in this state, the cover fitting member 170 is screw-joined with a sleeve 120, thereby fitting the cover member 130 thereto. After this, the cover member 130 is moved in the axial direction to separate the projection from the opening, thereby it becoming for the cover member 130 to turn round the axis. On one hand, the movement of the cover member 130 in the axial direction is restrained by the cover fitting member 170 and the slide restraint member 180 as well.

14 Claims, 5 Drawing Sheets

ENDOSCOPE

CROSS REFERENCE TO RELATED APPLICATIONS

The disclosure of Japanese Patent Application No. JP2004-23984, filed Jan. 30, 2004, entitled "ENDOSCOPE". The contents of that application are incorporated herein by reference in their entirety.

BACKGROUND OF THE INVENTION

The present invention relates to an endoscope including a plurality of cover members, of which each is arranged to cover a connection portion where the soft member constituting the insertion portion, cord, etc. of the endoscope is connected with the hard member constituting the control portion, connectors, etc. of the endoscope.

Description of the Related Art

The endoscope is generally composed of the following constituents, that is, an insertion portion which is inserted in the somatic cavity, a control portion successively connected with the base end portion of the insertion portion, and a connector connected with the control portion by means of the cord. The soft portion which constitutes the base end portion of the insertion portion and the cord are made of a soft member while the control portion and the connector are made of a hard member. The connection portion between the soft member and the hard member is covered with such a cover member that protects the soft member from being crushed or snapped. In general, this cover member is made of a resilient member such as rubber. FIG. 7 of the accompanying drawings is a schematic sectional view showing the connection portion between the insertion portion and the control portion and its surroundings of the conventional endoscope. A cylindrical member 10 constituting the soft portion is connected with a sleeve 20 constituting a part of the control portion. The cover member 30 is set to cover the outside of this connection portion.

The end portion of the cover member 30, which is positioned on the insertion portion side, comes in close contact with the outer surface of the cylindrical member 10. The inside surface near the center portion of the cover member 30 comes in contact with the end portion of the sleeve 20, and the airtightness of this portion is secured by a O-ring 40 which is arranged in the groove portion formed in the sleeve 20. A case member 50 is put on the outer circumference on the base end side of the cover member 30, and the airtightness of this portion is secured by a O-ring 42 which is arranged in the groove portion 34 formed on the outer circumference on the base end side of the cover member 30. A threaded portion is formed along the inner circumference of a portion where the groove portion 34 is formed. This threaded portion is screw-joined with the threaded portion formed on outer circumference of the sleeve 20, thereby the cover member 30 being joined together with the control portion. On one hand, the case member 50 is clamped immovably in the axial direction by means of a check ring 60 which is screw-joined with the threaded portion of the sleeve 20. In case of a certain cover member 30, the base end side member where the O-ring 42 is arranged, some threaded portion is formed and so forth, is made of a metallic material while the tip end side portion connected with that base end side member is made of a resilient material such as rubber.

As described above, in general, the cover member includes a threaded portion formed on the inner circumference surface of the based end portion. This threaded portion is screw-joined with the hard member thereby fixing the cover member to the hard member. As a related art with regard to the cover member, the Japanese Patent Laid-open Publication No. 2000-152910 discloses a cover member in which there is provided a restraint means making it impossible for the cover member to rotate.

By the way, in the process of cleaning the endoscope, it happens that the operator unintentionally turns the cover member while he wipes out water remaining on the cover member. However, in case of the cover member as shown in FIG. 7, since it is fix by the screw-joint, there is a possibility that the screw-joint is loosened, which in turn might cause airtight failure or the like.

Furthermore, in case of that which was disclosed by the above-mentioned publication, that is, in case of the endoscope provided with the restraint means a making it impossible for the cover member to rotate, when the operator strongly turns the cover member, especially the operator familiar with the conventional structure turns the cover member excessively, there is fear that structural parts might be broken.

SUMMARY OF THE INVENTION

The present invention has been made in view of the problems as described above and the object of the invention is to provide a novel and improved endoscope capable of preventing the cover member from being damaged and also preventing the airtight failure from being caused.

In order to solve the problems as described above, according to an aspect of the invention, there is provided an endoscope including a cover member detachably provided at a joint portion between a soft member and a hard member of the endoscope; and a cover fitting member which is arranged inside the cover member so as to relatively move in the axial direction with regard to the cover member and screw-joins with the outer circumference surface of the hard member thereby fitting the cover member thereto, wherein the cover fitting member is made detachable to the cover member in response to the relative movement of the cover member in the axial direction.

According to such a constitution as mentioned above, the cover fitting member is first joined with the cover member. Then, the cover fitting member is screw-joined with the hard member by turning the above joined cover fitting member and cover member as one body, thereby the cover member being fitted to the hard member. After fitting, the cover fitting member and the cover member are relatively moved in the axial direction, thus both of them being separated from each other. At the time of being separated, since the cover fitting member is arranged inside the cover member, the cover member is held in the state that it is fitted to the hard member, and it becomes possible for the cover member to turn with respect to the cover fitting member and the hard member as well.

To put it more concretely, the endoscope according to the invention may include a groove portion which is formed on and along the inner circumference surface of the cover member and wherein the cover fitting member is arranged so as to relatively move in the axial direction with regard to the cover member; a joint portion formed in the groove portion of the cover member; and a rotation restraint portion which is formed in the cover fitting member and detachably joins with the joint portion of the cover member in response to the relative movement of the cover member in the axial direction, thereby restraining the relative rotation to the cover member.

According to such a constitution as described above, when the rotation restraint portion joins with the joint portion, the cover fitting member and the cover member can rotate as one body. When the rotation restraint portion separates from the joint portion, the cover fitting member can rotate with respect to the cover member. In the joint state, if the cover fitting member and the cover member turn as one body to screw-join the cover fitting member with the hard member, it becomes possible to fit the cover member to the hard member. After fitting the cover member, if relatively moving the cover fitting member and the cover member in the axial direction and keeping them in the separate state, the cover member can freely turn with respect to the cover fitting member and the hard member. In this way, if the cover member is put in the separate state after fitting it, the cover member can turn round the axis. Therefore, the rotation of the cover member never loosens any connection in the endoscope, thus the airtightness being secured. Furthermore, since the rotation of the cover member after being fit is not restrained, if the operator turns round the cover member, there is no fear that the cover member and other structural parts are damaged.

An endoscope may further include a case member which is fitted to the outer circumference of the hard member so as to cover the outer circumference of the base end side of the cover member, wherein the cover fitting member plays an additional part as a fixing member for fixing the case member in the axial direction. Like this, since the cover fitting member is given an additional function, the number of parts can be reduced. Furthermore, it may be possible to further provide a restraint portion for restraining the movement range of the cover fitting member on the base end side in the axial direction.

It is preferable to further include a slide restraint member which restrains the movement of the cover member in the axial direction in order to hold the separate state between the cover member and the cover fitting member while the cover member is fitted to the hard member by the cover fitting member. With the provision of the slide restraint member, it becomes possible to surely prevent the cover member from relatively moving toward the cover fitting member to return to the joint state from the separate state. The slide restraint member may be made of a resilient material intervening between the cover member and the hard member. When the slide restraint member is made of the resilient member, it becomes possible to widen the range of the gap dimension, in other words, to make the allowance of a part dimension loose.

As has been described, in the endoscope according to the invention, it becomes possible to allow the cover member to turn round the axis and at the same time, to restrain the movement of the cover member in the axial direction. Therefore, it becomes possible for an operator of the endoscope to turn the cover member without causing any damage, thus the airtightness being protected from any leakage.

DETAILED DESCRIPTION OF THE PREFERRED EMBODIMENTS

Figure 1:
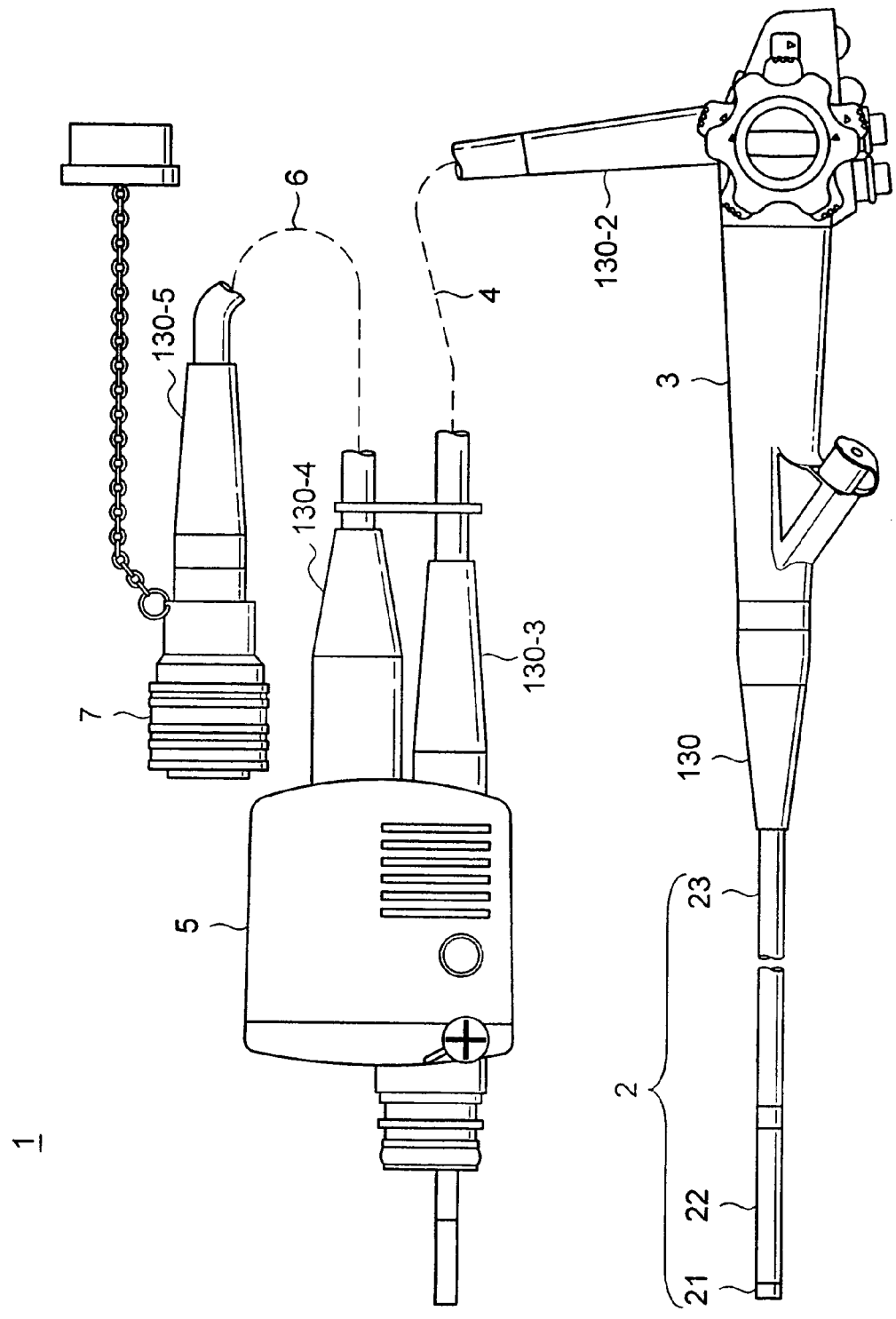
FIG. 1 illustrates in exploded view main portions of an endoscope according to the invention in order to schematically showing the whole construction of it.

The invention will now be described in detail by way of some preferred embodiments with reference to the accompanying drawings. In the following description and drawing, a constituent of the invention having substantially like function and constitution is designated by a like reference numeral or sign, thereby omitting repetitive redundant explanation about such constituent.

As will be seen from FIG. 1 schematically showing the whole construction of the endoscope 1, the endoscope 1 is composed of an insertion portion 2, a control portion 3 with which the base end portion of the insertion portion 2 is connected, and connector portions 5 and 7 connected with a universal cord 4 which are branching off from the control portion 3. The insertion portion 2 is composed of a tip distal end portion 21, a flexible bending portion 22 and a soft portion 23 forming the base end portion of the insertion portion 2, all of which are connected with each other in sequence in this order. The control portion 3 is used for carrying out the remote control of the curvature relating to the bending portion 22. Two connector portions 5 and 7 are connected with each other by mean of a cord 6.

The soft portion 23 is made of a soft member while the control portion 3 is made of a hard member. The soft portion 23 and the control portion 3 are connected with each other and the outer surface of this connection portion is covered by a detachable cover member 130. For example, this cover member may be made of a resilient member such as rubber to prevent the soft portion from being crushed or snapped. In the same manner as the above, the outer surface of each connection portion is covered by a corresponding detachable cover member. To put it more concretely, the outer surface of the connection portion between the control portion 3 and the universal cord 4 is covered by a cover member 130-2; the outer surface of the connection portion between universal cord 4 and the connector portion 5 is covered by a cover member 130-3; the outer surface of the connection portion between the connector portion 5 and the cord 6 is covered by a cover member 130-4; and the outer surface of the connection portion between the cord 6 and the connector portion 7 is covered by a cover member 130-5.

Figure 2:
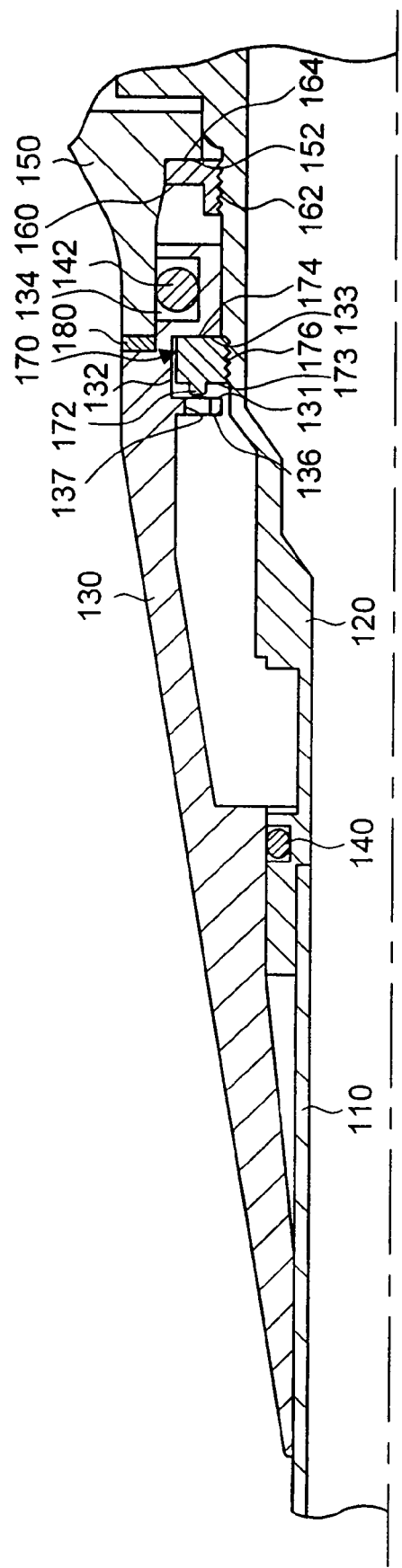
FIG. 2 is a schematic sectional view showing the important part of an endoscope according to the first embodiment of the invention.

In the following, an endoscope according to the first embodiment of the invention will be described in detail with reference to FIG. 2. This figure is a schematic sectional view (only the upper half with regard to the center axis) showing the cover member 130 and its circumference according to the first embodiment of the invention. In the following description, the direction going toward the side of the insertion portion 2 along the center axis is referred to as "front side or direction" while the direction going toward the side of the control portion 3 (base end side) along the center axis is referred to as "rear or back side or direction."

The soft portion 23 forming the base end portion of the insertion portion 2 is made up of a cylindrical member 110. This cylindrical member 110 is connected with a sleeve 120 which is a part of the control portion 3. The cylindrical member 110 is made of a soft member while the sleeve 120 is made of a hard member. The cover member 130 is provided such that it covers the outside of the connection portion between the cylindrical member 110 and the sleeve 120. The front end potion of the cover member 130 closely comes in contact with the outer surface of the cylindrical member 110. The inner surface near the center portion of the cover member 130 comes in contact with the outer surface of the front end portion of the sleeve 120. A groove portion is formed at this contact portion along the outer circumference of the sleeve 120 and an O-ring 140 is pressed into this groove portion, thereby the airtightness being secured.

The outer surface of the rear end portion of the cover member 130 comes in contact with the inner surface of the front end portion of a case member 150 that is one constituent of the control portion 3. The case member 150 is put on the outer circumference of the control portion 3 so as to cover the outer circumference of the rear side (base end side) of the cover member 130. In this contact portion of the cover member 130 and the case member 150, a groove portion 134 is formed on the outer circumference of the cover member 130 and an O-ring 142 is pushed into that groove portion 134. A step portion is formed such that the groove portion 134 sees it standing adjacent thereto on the front side. The case member 150 makes contact with the step portion and at the same time presses the O-ring 142, thereby securing airtightness.

A slide restraint member 180 is put in a gap between the tip portion of the case member 150 and the side surface of the step portion of the cover member 130. In other words, the slide restraint member 180 interposes between the cover member 130 and the case member 150. The slide restraint member 180 is a restraint member for restraining the movement of the cover member 130 in the axial direction. The slide restraint member 180 may have a ring form or a form of a letter "C" and may be made of such a resilient member as rubber or made of a hard member. When the slide restraint member 180 is made of the resilient member, it becomes possible to widen the range of the gap dimension, in other words, to make the allowance of a part dimension loose.

In the cover member 130, a groove portion 132 is formed on the inner circumference surface in front the groove portion 134 so as to be along that circumference direction. A step portion is formed in front of the groove portion 132 such that the inner diameter is gradually enlarged. With this structure, there is formed an inner wall 136 which projects toward the center axis and goes around so as to form the front side wall of the groove portion 132. A plurality (two, for instance) of openings 137 are formed, at an equal interval, on the circumference of a front side surface 131 which is the side surface of the front side (front end side) of the groove portion 132. The opening 137 is one of the examples of a joint portion.

A cover fitting member 170 is provided inside the groove portion 132. The cover fitting member 170 is a member for fitting the cover member 130 to the endoscope. The cover fitting member 170 is arranged such that it can freely move inside the groove portion 132, in other words, within a predetermined range, in the axial direction relative to the cover member 130. The cover fitting member 170 is provided with a threaded portion 176 which allows a thread-coupling with a hard member. The threaded portion 176 can make the thread-coupling with the hard member while it is staying inside the groove portion 132, thus the cover fitting member 170 comes to be fixed to the hard member. Furthermore, the cover fitting member 170 includes a rotation restraint portion (for example, a projection 172 (described later)) capable of being inserted in the opening 137 formed in the groove portion 132). The rotation restraint portion joins with the cover member 130 and restrains the rotation of the cover member 130 relative to the cover fitting member 170. Accordingly, when fitting the cover member 130 to the hard member, the cover member 130 is first united with the cover fitting member 170 and is then fitted to the hard member by rotating this united body. On the other hand, after applying the cover member 130 to a predetermined connection portion to be covered, if the cover member 130 and the cover fitting member 170 are detached from each other, the cover member 130 comes to freely rotate unrelated to the cover fitting member 170. Accordingly, once having fitted the cover member 130 to the predetermined portion, it is never happened that the cover member 130 comes off its once fitted place by its rotation, because the cover fitting member 170 is still functions as the rotation restraint member.

Figure 7:
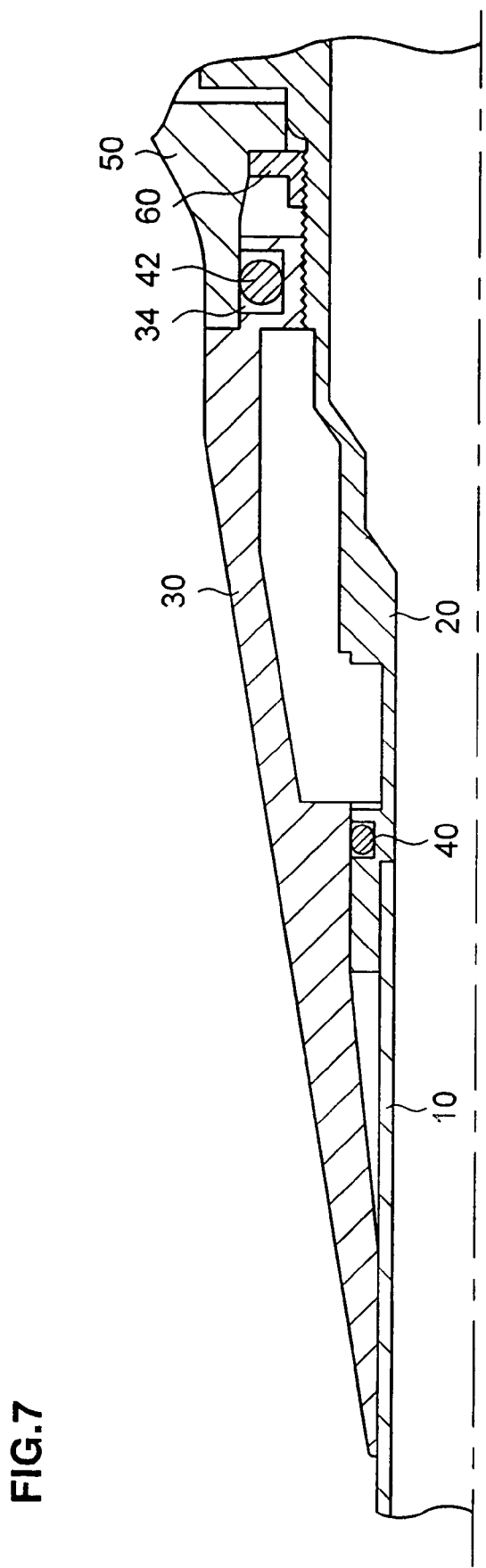
FIG. 7 is a schematic sectional view showing the important part of a conventional endoscope.

Now, let us put the above cover fitting member 170 more concretely. The cover fitting member 170 is made of a cylindrical member and includes the threaded portion 176 that is formed along its inner circumference surface. This threaded portion 176 can mate with another threaded portion that is formed along the outer circumference of the sleeve 120. With this mating of two threaded portions, the cover fitting member 170 is fitted to the sleeve 120, thus the cover member 130 being fitted to the sleeve 120 with the help of the cover fitting member 170. The cover member 130 according to this embodiment is different from the related art cover member 30 as shown in FIG. 7 on the point that the former has no threaded portion to mate with other member. Because of this, even if the cover member 130 is rotated around the axis, it will not make any motion in the axial direction.

On the circumference of the front surface 173 of the cover fitting member 170, a plurality of projections 172 is formed such that they are arranged at an equal interval in the circumferential direction. The number of projections 172 may be two, for instance. The front surface 173 is the opposite surface of the front side surface 131 and the projection 172 is formed to opposite to the opening 137. The number of projections 172, the intervals between projections as formed and the number of openings 137 and the intervals between openings as formed are made equal to each other, respectively. The length in the axial direction of the cover fitting member 170 including the projection 172 is made shorter than the same of the groove portion 132. The projection 172 is inserted in or drawn out from the corresponding opening 137 according to the relative movement in the axial direction between the cover member 130 and the cover fitting member 170. In this way, the cover member 130 and the cover fitting member 170 are detachably constructed.

In the state where the projection 172 is inserted in the opening 137 (i.e. joint state), it is impossible for the cover member 130 to rotate round the axis relative to the cover fitting member 170 while the cover fitting member 170 and the cover member 130 can rotate together as one body. On one hand, as shown in FIG. 2, in the state where the projection 172 and the opening 137 are separated from each other (i.e. separate state), it becomes possible for the cover member 130 to rotate round the axis relative to the cover fitting member 170. As described above, the projection 172 is inserted in or extracted from the opening 137, thereby functioning as a rotation restraint portion that restrains the relative rotation of the cover member 130 and the cover fitting member 170 around the axis.

A check ring 160 is provided on the rear side of the cover member 130. The check ring is one of the examples of a fixing member. There is formed along the inner circumferential surface a threaded portion 162 which mates with another threaded portion formed along the outer circumferential surface of the sleeve 120, thereby the check ring 160 is connected with the sleeve 120. The rear side surface 164 of the check ring 160 comes in contact with the side surface 152 of a step portion formed on the inner circumference of a case member 150. With this, the case member 150 is fixed in the axial direction.

In the following, there is explained a method of fitting the cover member 130 to the endoscope and the operation of the same as well. First of all, before fitting the cover member 130 to the endoscope, the endoscope is set in the following state where the cylindrical member 110 and the sleeve 120 are connected while the case member 150 is fixed in the axial direction by means of the check ring 160. Then, the cover member 130 is fitted to the endoscope according to the following steps of: putting the cover fitting member 170 in the groove portion 132 of the cover member 130; inserting the projection 172 in the opening 137 to mate them with each other; fitting the cover member 130 and the cover fitting member 170 as mated with each other to the endoscope in the above state; and turning both of the cover member 130 and the cover fitting member 170 round the axis as one body to mate the threaded portion 176 of the cover fitting member 170 with the threaded portion of the sleeve 120. In the steps as mentioned above, the cover fitting member 170 is fixed to the sleeve 120 while the cover member 130 gets in the state where it is fitted to the hard member.

In the next, only the cover member 130 is moved toward the front side in the axial direction to separate the projection 172 from the opening 137. At this time, the rear side surface 133 of the groove portion 132 comes in contact with the rear surface 174 of the cover fitting member 170, thereby the movement of the cover member 130 toward the front side in the axial direction being restrained. Finally, in order to keep the projection 172 separated from the opening 137, a slide restraint member 180 is put in a gap between the side surface of the stepped portion of the outer circumference at the rear end of cover member 130 and the front end of the case member 150. Accordingly, the movement of the cover member 130 to the rear end in the axial direction is restrained, thus the projection 172 being prevented from again entering in the opening 137.

As described above, after fitting the cover member 130 to the endoscope, since the projection 172 and the opening 137 are kept in the separate state, it becomes possible for the cover member 130 to freely turn round the axis. Furthermore, since the cover member 130 is restrained by the cover fitting member 170 and the slide restraint member 180, it becomes impossible for the cover member 130 to move in the axial direction. Therefore, the rotation of the cover member 130 never loosens any connection in the endoscope, thus the airtightness being secured. In case of the conventional endoscope of the type wherein the rotation of the cover member is restrained, it has happened that the endoscope is broken by an operator who rotates the cover member by force. However, in case of the cover member according to the present embodiment of the invention, there is no fear of giving such damage to the endoscope.

Figure 3:
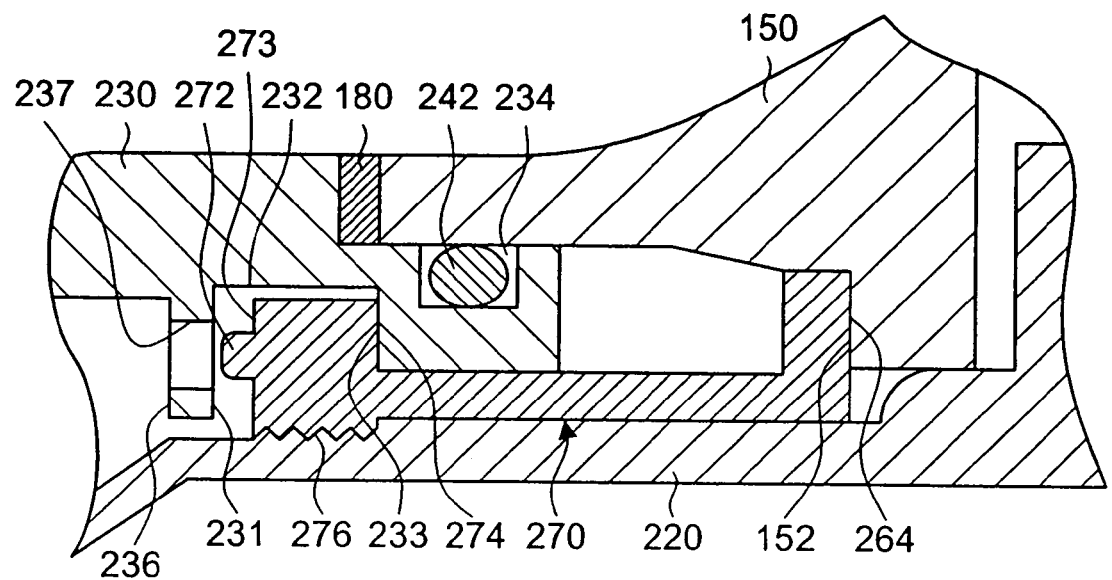
FIG. 3 is a schematic sectional view showing the important part of an endoscope according to the second embodiment of the invention.

In the next, an endoscope according to the second embodiment of the invention will be described in detail with reference to FIG. 3. This figure is a schematic sectional view showing a cover fitting member 270 and its circumference according to the second embodiment of the invention. Comparing this figure with FIG. 2, it will be seen that FIG. 3 is the figure that is obtained by separating only the rear part of the FIG. 2 and enlarging it. In the second embodiment, there is adopted the cover fitting member 270 that is constructed by integrating the cover fitting member 170 with the check ring 160 in the first embodiment. Accordingly, in the following, there will be omitted repetitive similar explanation related to the like constitution as adopted in the first embodiment.

The cover fitting member 270 according to the second embodiment has an integrated structure which is made up of a cylindrical portion which lies between the cover fitting member 170 and the check ring 160 to connect them with each other, both of them being adopted in the first embodiment. That is, as shown in FIG. 3, the cover fitting member 270 has a form including two projections projecting uprightly from both of the front end and the rear end of it, in other words, a flange-like form, of which the section would show a shape similar to Chinese Kanji 凹. The cover fitting member 270 includes a threaded portion 276 formed on the inner circumference surface of its front end portion. This threaded portion 276 is screw-joined to another threaded portion formed on the outer circumference surface of the sleeve 220, thus the cover fitting member 270 being fixed to the sleeve 220.

Furthermore, the front end portion of the cover fitting member 270 is arranged inside the groove portion 232 of a cover member 230 such that it can move relatively in the axial direction. On the circumference of the front surface 273, a plurality (two, for instance) of projections 272 as rotation restraint portion is formed such that they are arranged at an equal interval in the circumferential direction. The rear surface 264 of the rear end portion of the cover fitting member 270 comes in contact with the side surface 152 of the step potion of the case member 150 and fixes this case member 150 in the axial direction. The inner surface of the cylindrical portion between the front end portion and the rear end portion of the cover fitting portion 270 comes in contact with the sleeve 220 while the outer surface of the same comes in contact with the cover member 230.

Approximately similar to the first embodiment, a groove portion 234 is formed on the outer circumference of the rear end portion of the cover member 230. On the front side of the groove portion 234, a step portion is formed along the outer circumference adjacent to the groove portion 234. In this case, however, since the cylindrical portion of the cover fitting portion 270 is located between the cover member 230 and the sleeve 220, the inner diameter of the portion where the groove portion 234 is formed is made larger than that of the portion where groove portion 134 is formed according to the first embodiment. Except this point, the cover member 230 has the same constitution as the cover member 130 according to the first embodiment To put it more concretely, the front side surface 231, the groove portion 232, the rear side surface 233, the inner wall 236, and the opening 237 are formed in the same way as the front side surface 131, the groove portion 132, the rear side surface 133, the inner wall 136, and the opening 137 are formed in the first embodiment. The opening 237 functions as a mating portion in the same way as the opening 137 according to the first embodiment functions.

Similar to the first embodiment, an O-ring 242 is pushed into the groove portion 234 in order to secure the airtightness. The case member 150 comes in contact with the step portion adjacent to the groove 234 and, at the same time, presses the O-ring 242. A slide restraint member 180 is put in a gap between the tip portion of the case member 150 and the side surface of the step portion of the cover member 230. The slide restraint member 180 is a restraint member for restraining the movement of the cover member 230 in the axial direction.

The front end portion of the cover fitting member 270 is arranged inside the groove portion 232, and the cover fitting member 270 can freely move relative to the cover member 230 within a predetermined range in the axial direction. Similar to the first embodiment, the projection 272 is inserted in or extracted from the opening 237 in response to this relative movement. The insertion and extraction movement of the projection 272 with respect to the opening 237 causes the cover member 230 to be connected with or separated form the cover fitting member 270. In the state where the projection 272 is inserted in the opening 237 (i.e. joint state), it is impossible for the cover member 230 to turn round the axis relative to the cover fitting member 270 while the cover fitting member 270 and the cover member 230 can rotate together as one body. On one hand, as shown in FIG. 3, in the state where the projection 272 and the opening 234 are separated from each other (i.e. separate state), it becomes possible for the cover member 230 to turn round the axis relative to the cover fitting member 270. Furthermore, in the separate state, the rear surface 274 of the front end portion of the cover fitting member 270 comes in contact with the rear side surface 233 of the groove portion 232 of the cover member 230.

The sleeve 220 includes a threaded portion as formed only at a place where it screw-joins with the front end portion of the cover fitting member 270 while it includes no threaded portion at a place where it comes in contact with the rear end portion of the cover fitting member 270. The other structure of the sleeve 220 is the same as that of the sleeve 120 according to the first embodiment.

Similar to the first embodiment, fitting the cover member 230 to the endoscope is carried out according to the following steps, which are: inserting the projection 272 in the opening 237 thereby producing the joint state between the cover member 230 and the cover fitting member 270; turning both of the cover member 230 and the cover fitting member 270 as one body round the axis to screw-join the cover fitting member 270 with the sleeve 220; and then moving the cover member 230 toward the front side in the axial direction thereby separating the projection 272 from the opening 237. At this time, the rear end surface 233 of the cover member 230 comes in contact with the rear surface 274 of the cover fitting member 270, thereby the movement of the cover member 230 in the axial direction being restrained. Finally, the slide restraint member 180 is put in the gap between the case member 150 and the side surface of the step portion at the outer circumference in the rear end portion of the cover member 230.

As has been described above, since the cover member 230 after being fitted to the endoscope is in the separate state, it can freely turn round the axis. Furthermore, the cover member 230 is restrained by the cover fitting member 270 and the slide restraint member 180 as well, it becomes impossible for the cover member 230 to move in the axial direction. Therefore, the second embodiment provides the same effect as that obtained by the first embodiment. Still further, in the second embodiment, the cover fitting member 270 can play a part as the check ring 160 which is one of the examples of a fixing member, thus the effect that the number of parts is reduced being obtained.

Figure 4:
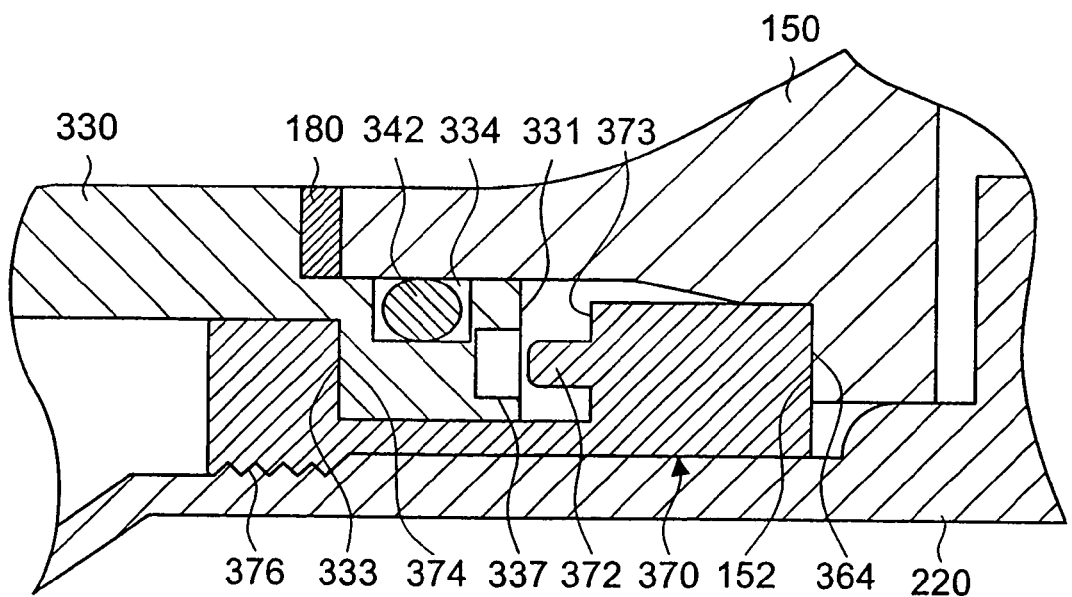
FIG. 4 is a schematic sectional view showing the important part of an endoscope according to the third embodiment of the invention.

In the next, an endoscope according to the third embodiment of the invention will be described in detail with reference to FIG. 4. This figure is a schematic sectional view showing a cover fitting member 370 and its circumference according to the third embodiment of the invention. Comparing this figure with FIG. 2, it will be seen that FIG. 4 is the figure that is obtained by separating only the rear part of the FIG. 2 and enlarging it. In the third embodiment, there is adopted the cover fitting member 370 that is constructed by integrating the cover fitting member 170 with the check ring 160 in the first embodiment. However, a connective position at which the cover member 330 and the cover fitting member 370 are connected with each other is made different from that which has been adopted in the first embodiment. In the following, the explanation will be made paying attention to these points but omitting in part the repetitive explanation about the similar constitution as already described in the first and second embodiments.

As shown in FIG. 4, the cover fitting member 370 according to the third embodiment has a form including two projections projecting uprightly from both of the front and the rear ends of it, in other words, a flange-like form, of which the section shows a shape similar to a Chinese Kanji 凹. A threaded portion 376 is formed on the inner circumference surface of the front end portion of the cover fitting member 370. The threaded portion 376 screw-joins with a threaded portion formed on the outer circumference surface of the sleeve 220, thereby fixing the cover fitting member 370.

The front end portion of the cover fitting member 370 is arranged inside the cover member 330 such that it can move relatively in the axial direction. On the circumference of the front surface 373 of the rear end portion of the cover fitting member 370, a plurality (two, for instance) of projections 372 as rotation restraint portion is formed such that they are arranged at an equal interval in the circumferential direction. The rear surface 364 of the rear end portion of the cover fitting member 370 comes in contact with the side surface 152 of the step potion of the case member 150 and fixes this case member 150 in the axial direction. The inner surface of the cylindrical portion between the front end portion and the rear end portion of the cover fitting member 370 comes in contact with the sleeve 220 while the outer surface of the same comes in contact with the cover member 330.

Roughly speaking, the structure of the cover member 330 according to the third embodiment can be derived from the cover member 230 according to the second embodiment, that is, the cover member 330 is derived from the cover member 230 by transferring the position of the opening 237 to the most rear end portion and further deleting the inner wall 236. In the following, the structure of the cover member 330 will be described more in detail. The cover member 330 includes a groove portion 334 which is formed in the outer circumference surface of its rear end portion. The cover member 330 also includes a step portion with is formed along the outer circumference adjacent to the front side of the groove portion 334. An O-ring 342 is put in the groove 334 in order to secure the airtightness. The case member 150 comes in contact with the step portion and, at the same time, presses the O-ring. A slide restraint member 180 intervenes between the tip end of the case portion 150 and the side surface of the step portion of the cover member 330. This slide restraint member 180 works as a restraint member for restraining the movement of the cover member 330 in the axial direction.

A step portion is formed in the inner circumference which is adjacent to the groove portion 334 of the cover member 330 such that the inner diameter is gradually enlarged. The front end portion of the cover fitting member 370 is arranged in the inside of this step portion, and the side surface 333 of the step portion comes in contact with the front surface 374 of the rear end portion of the cover fitting member 370.

On one hand, the rear surface 331 of the cover member 330 opposes to the front surface 373 of the cover fitting member 370. Furthermore, on the circumference of the rear surface 331 of the cover member 330 opposing to the projection 372 of the cover fitting member 370, a plurality (two, for instance) of openings 337 are formed at an equal interval along the circumferential direction. The number of openings 337 and the intervals between openings as formed are made equal to those of projection 372. Similar to the opening 137 as described in the first embodiment, the opening 337 also functions as a joint portion.

Similar to the first embodiment, the cover fitting member 370 can freely move relative to the cover member 330 within a predetermined range in the axial direction. According to this relative movement, the projection 372 is inserted in or extracted from the opening 337, thus the cover member 330 and the cover fitting member 370 being detachably joined with each other. In the state where the projection 372 is inserted in the opening 337 (i.e. joint state), it is not possible for the cover member 330 to turn round the axis with regard to the cover fitting member 370, but it possible for both the cover fitting member 370 and the cover member 330 to turn round as one body. As shown in FIG. 4, on one hand, in the state where the projection 372 is separated from the opening 337 (i.e. separate state], it becomes possible for the cover member 330 to turn round the axis with regard to the cover fitting member 370. Furthermore, in the separate state, the rear surface 374 of the front end portion of the cover fitting member 370 comes in contact with the side surface 333 of the step portion of the cover member Similar to the first embodiment, fitting the cover member 330 to the endoscope is carried out according to the following steps, which are: inserting the projection 372 in the opening 337 thereby producing the joint state between the cover member 330 and the cover fitting member 370; turning both of the cover member 330 and the cover fitting member 370 as one body round the axis to screw-join the cover fitting member 370 with the sleeve 220; and then moving the cover member 330 toward the front side in the axial direction thereby separating the projection 372 from the opening 337. At this time, the side surface 333 of the cover member 330 comes in contact with the front surface 374 of the cover fitting member 370, thereby the movement of the cover member 330 in the axial direction being restrained. Finally, the slide restraint member 180 is put in the gap between the case member 150 and the side surface of the step portion at the outer circumference in the rear end portion of the cover member 330.

As has been described above, since the cover member 330 after being fitted to the endoscope is in the separate state, it can freely turn round the axis. Furthermore, the cover member 330 is restrained by the cover fitting member 370 and the slide restraint member 180 as well, it becomes impossible for the cover member 330 to move in the axial direction. Therefore, the third embodiment provides the same effect as that obtained by the first embodiment. Still further, in this third embodiment, the cover fitting member 370 can play a part as the check ring 160 which is one of the examples of a fixing member, thus the effect that the number of parts is reduced being obtained.

In the first through third embodiments, since the cover fitting member is screw-joined with the sleeve, it happens that, depending on the range (length) of the threaded portion, the cover fitting member is unnecessarily moved rearward when it is turned round the axis. The fourth and fifth embodiments as described in the following are made by taking the point as mentioned above into consideration.

Figure 5:
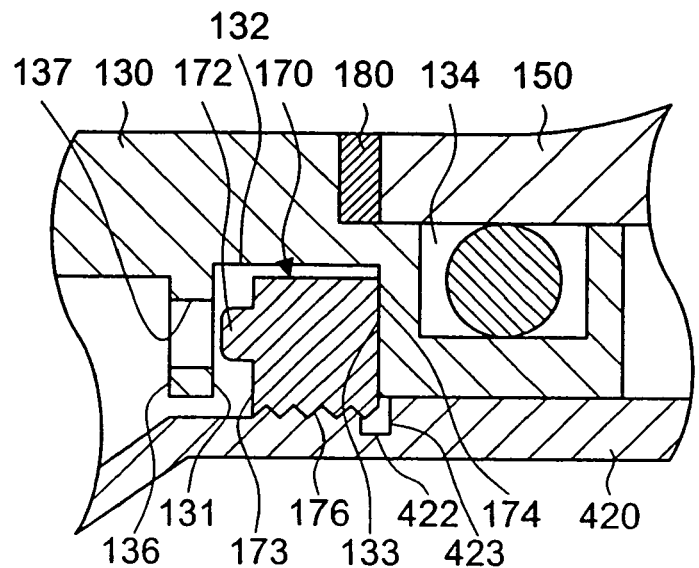
FIG. 5 is a schematic sectional view showing the important part of an endoscope according to the fourth embodiment of the invention.

An endoscope according to the fourth embodiment will now be described in detail with reference to FIG. 5, which is an enlarged view showing the important part of an endoscope according to the fourth embodiment of the invention. The feature of the fourth embodiment is that the sleeve is provided with a restraint portion in addition to the constitution of the first embodiment. The fourth embodiment is different form the first embodiment with regard to only the sleeve. That is, in the fourth embodiment, there are used the same members as used in the first embodiment except the sleeve. In the following, therefore, the description will be made by putting stress on the points which are different from the first embodiment, omitting the repetitive descriptions about the same constitution as the first embodiment.

A sleeve 420 of the fourth embodiment includes a groove portion 422 which is formed at the portion adjacent to the rear end of the screw-joint portion with which the threaded portion of the cover fitting member 170 screw-joins. In the sleeve 420, the outer surface adjacent to the rear end of the groove portion 422 becomes a contact surface coming in contact with the inner surface of the groove 134 of the cover member 130. A step portion 423 is formed from the groove portion 422 to the contact surface such that the outer diameter becomes lager than the inner diameter of the cover fitting member 170. Accordingly, even though the cover fitting member 170 moves rearward by screw-joining with the sleeve 420, it comes in contact with the step portion 423 and its further rearward movement is restrained. In this way, the step portion 423 functions as a restrain portion restraining the rearward movement range in the axis direction i.e. toward the base end side. According to the fourth embodiment, therefore, in addition to the effect obtained by the first embodiment, there is obtained the effect that the cover fitting member is prevented from unnecessarily moving rearward.

Figure 6:
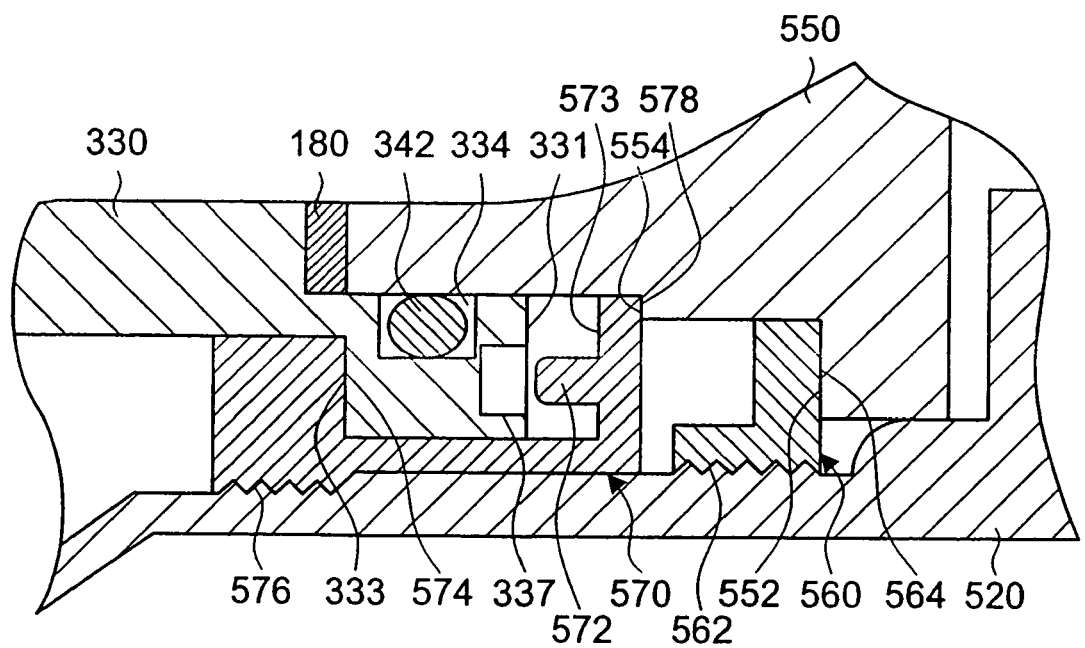
FIG. 6 is a schematic sectional view showing the important part of an endoscope according to the sixth embodiment of the invention.

An endoscope according to the fifth embodiment will now be described in detail with reference to FIG. 6, which is an enlarged view showing the important part of an endoscope according to the fifth embodiment of the invention. The feature of the fifth embodiment is that the case member is provided with a restraint portion, by which the rearward movement of the cover fitting member is restrained. The endoscope according to the fifth embodiment is constituted by using the cover member 330 according to the third embodiment as shown in FIG. 4. In the following, the description will be made with regard to the points which are different from the third embodiment, omitting the repetitive descriptions about the same constitution as the third embodiment.

The cover fitting member 570 of the fifth embodiment has the same section as that of the cover fitting member 370 according to the third embodiment, to put it more concretely, a shape similar to Chinese Kanji 凹. The thickness in the axial direction of the rear end portion of the cover fitting member 570 is made thinner than that of the cover fitting member 370. Except the above difference between the above two cover fitting members, the cover fitting member 570 has the same constitution as the cover fitting member 370 according to the third embodiment. There is formed at the inner circumference of the front end portion of the cover fitting member 570, a threaded portion 576 which screw-joins with the threaded portion formed on the outer circumference of the sleeve 520 to fix the cover fitting portion 570.

The rear surface 574 of the front end portion of the cover fitting member 570 comes in contact with the side surface 333 of the step portion of the cover member 330. Similar to the projection 372 of the third embodiment, a plurality (two, for instance) of projections 572 are provided at an equal interval on the circumference of the front surface 573 of the rear end portion of the cover member 570 along the circumferential direction. Similar to the projection 372 of the third embodiment, the projection 572 functions as a restraint portion restraining the rotation of the cover member 330 round the axis.

In the inner surface of a case member 550 according to the fifth embodiment, a step portion 554 is formed by enlarging the inner diameter on the rear side. The step portion 554 is provided such that it comes in contact with the rearward surface of 578 of the rear end portion of the cover fitting member 570. According to the fifth embodiment, even if the cover fitting member 570 tries to move rearward, with the help of the screw-joint action, the rear surface 578 of the cover fitting member 570 comes in contact with the side surface of the step portion 554 to restrain the further rearward movement of the cover fitting member 570. Like this, the step portion 554 functions as a restraint portion restraining the rearward movement range in the axis direction i.e. toward the base end side In the fifth embodiment, a check ring 560 for securing the case member 550 is provided behind the cover fitting member 570. The check ring 560 has the same constitution as the check ring 160 and also includes a threaded portion 562 as formed along its inner circumference. The check ring 560 is fixed to the sleeve 520 by having the threaded portion 562 screw-joined with the threaded portion formed on the outer circumference of the sleeve 520. The rear surface 564 of the check ring 560 comes in contact with the side surface 552 of the step portion formed in the inner circumference of the case member 550 to fix the case member 550 in the axial direction.

As described above, according to the fifth embodiment, in addition to the effect obtained by the third embodiment, there can be further obtained the effect that the cover member is prevented from unnecessarily moving rearward. Furthermore, according the fifth embodiment, the thickness of the rear end portion of the cover fitting member can be made thinner comparing with the case of the third embodiment.

In the respective embodiments having been described so far, an adhesive may be applied to the screw-joint portion of the cover fitting member in order to prevent the screw-joint from being loosened. A buffering material having a low friction coefficient may intervene between the cover fitting member and the cover member which come in contact with each other. For example, DELRIN (Registered TM, available from Dupont), POM (polyether imide) and so forth belong to such buffering materials. Furthermore, it may be possible to give a lubrication process to either the cover fitting member or the cover member or both at a contact portion where they come in contact with each other. For example, plating process using a lubricant, application of lubricant grease and so on may be adoptable as the lubrication process. Accordingly, this lubrication process makes it possible for the cover member to easily turn with regard to the cover fitting member, and also makes it possible for the cover fitting member to be prevented form being rotated by the friction at the contact portion between the cover fitting member and the cover member.

In the respective embodiments having been described so far, each member such as a cover member, a cover fitting member, a sleeve, etc. may be made up of a plurality of parts. For example, it is possible to first assemble each member by using a plurality of parts according to the predetermined assembling order and then, to finally integrate them by means of screws, adhesives, and so forth. In this case, a plurality of parts constituting a cover member, a cover fitting member, a sleeve, etc. may be made of materials which are identical to each other or may be different from each other. In case of the cover member, for example, the material forming the base end portion (ring body) in which the O-ring is arranged is made of a metal while the material forming the tip end side portion (cover rubber) connected with the tip end is made of a resilient material such as rubber. The base end side portion and the tip end side portion may be integrally formed or integrated by using screws, adhesives, and so on. In this case, for example, if the rear side surfaces 133, 233 of the cover members as shown in FIGS. 2, 3, and 5 and the side surface 333 of the step portion as shown in FIGS. 4 and 6 are constituted by the end surface of the base end side portion, the assembly of the cover member is made easy by inserting the cover fitting member in the groove portion of the cover member. Furthermore, in the respective embodiments having been described so far, it is not always necessary for the opening to be s a through-hole.

While several preferred embodiments of the invention have been shown and described with reference to the accompanying drawings, it is needless to say that the invention is not always limited to such embodiments. It will be apparent that one who is skilled in the art can make various changes and modifications without departing from the principle and spirit of the invention, the scope of which is defined in the appended claims, and it is understood that those changes and modifications naturally belong to the technical scope of the invention.

For example, in the respective embodiments having been described so far, the invention has been described with regard to the cover member 130 which is fitted to the portion at which the insertion portion and the control portion are connected with each other. However, the invention is not limited to this but is applicable to cover members 130-2, 130-3, 130-4 and 130-5 as shown in FIG. 1, and also applicable to the joint portion between other soft member and the hard member. Furthermore, the invention is applicable to the cover member fitted to a medical treatment tool.

Furthermore, in the respective embodiments having been described so far, the invention has been described by way of example where the joint portion is an opening while the rotation restraint portion is a projection. However, the invention is not limited to this example. It is possible to adopt the other constitution, for example a joint portion of the notched type or the like. Furthermore, the above description has been made about the case where the number of the joint portions and the projections is two, respectively. However, the number of the joint portions and the projections is not limited to such a fixed number. They may be one each and 3 or more each. Still further, it is not always needed for the joint portions and the projections are formed at an equal interval on the circumference.

As has been described, in the endoscope according to the invention, it becomes possible to allow the cover member to turn round the axis and at the same time, to restrain the movement of the cover member in the axial direction. Therefore, it becomes possible for an operator of the endoscope to turn the cover member without causing any damage, thus the airtightness being protected from any leakage.

What is claimed is:

1. An endoscope comprising:
 a cover member detachably provided at a joint portion between a soft member and a hard member of the endoscope, the cover member covering a portion of an outer surface of the soft member and a portion of an outer surface of the hard member in a radial direction of the soft and hard members, the cover member having neither a threaded portion nor a groove to mate with the soft and hard members; and
 a cover fitting member which is arranged inside the cover member, the cover fitting member covering a portion of an outer circumference surface of the hard member and screw-joining with the outer circumference surface of the hard member thereby fitting the cover member thereto, the cover member being movable in the axial direction with regard to the cover fitting member between a first position and a second position;
 wherein, in the first position, the cover member is restrained from rotating with respect to the cover fitting member, and in the second position, the cover member is freely rotatable with respect to the cover fitting member.

2. The endoscope as claimed in claim 1, further comprising:
a groove portion formed on and along an inner circumference surface of the cover member, the cover fitting member being arranged so as to relatively move in the axial direction with regard to the cover member;
a joint portion formed in a groove portion of the cover member; and
a rotation restraint portion which is formed in the cover fitting member,
when the cover member maintains to be provided on the joint portion and to cover the soft member and the hard member both at the first position and at the second position, and
wherein, when the cover member is at the first position, the rotation restrained portion mates with the joint portion, thereby restraining the cover member from rotating with respect to the cover fitting member, and
wherein, when the cover member is at the second position, the rotation restrained portion is separated from the joint portion, so that cover member is freely rotatable with respect to the cover fitting member.

3. An endoscope as claimed in claim 2 further comprising:
a case member which is fitted to the outer circumference of the hard member so as to cover an outer circumference of the a base end side of the cover member;
wherein the cover fitting member plays an additional part as a fixing member for fixing the case member in the axial direction.

4. An endoscope as claimed in claim 2, wherein there is provided a restraint portion restraining the movement range of the cover fitting member on the base end side in the axial direction.

5. The endoscope as claimed in claim 1, further comprising a slide restraint member which restrains the movement of the cover member in the axial direction in order to hold a separate state between the cover member and the cover fitting member while the cover member is fitted to the hard member by the cover fitting member.

6. The endoscope as claimed in claim 5, wherein the slide restraint member is made of a resilient member interposed between the cover member and the hard member.

7. The endoscope as claimed in claim 1, wherein a buffer material intervenes in a contact portion where the cover fitting member and the cover member come in contact with each other.

8. The endoscope as claimed in claim 1, wherein a lubrication process is given to the cover fitting member and/or the cover member at a contact portion where they come in contact with each other.

9. The endoscope as claimed in claim 1, wherein the cover fitting member has a threaded portion that contacts a corresponding threaded portion on the outer circumference surface of the hard member, the threaded portion of the cover fitting member being formed along its inner circumference surface.

10. The endoscope as claimed in claim 1, wherein a first end portion of the cover member comes in contact with the outer surface of the soft member, and a second end portion of the cover member comes in contact with the outer surface of the hard member.

11. The endoscope as claimed in claim 1 wherein the cover fitting member has a first circumference surface and a second circumference surface opposite to the first circumference surface, the first circumference surface facing an inner circumference surface of the cover member, the second circumference surface being in contact with the portion of the outer circumference surface of the hard member.

12. The endoscope as claimed in claim 2, wherein:
the joint portion includes an opening formed on a side circumference surface of the cover member, which extends in the axial direction;
the rotation restraint portion includes a projection formed on a side circumference surface of the cover fitting member, which extends in the axial direction;
when the cover member is at the first position, the projection is inserted in the opening; and
when the cover member is at the second position, the projection is separated from the opening.

13. The endoscope as claimed in claim 12, wherein the joint portion includes a plurality of openings formed at an equal interval on the side circumference surface of the cover member, and the rotation restraint portion includes a corresponding number of projections formed on the side circumference surface of the cover fitting member, which extends in the axial direction.

14. The endoscope as claimed in claim 1, wherein, when the cover member moves in the axial direction with regard to the cover fitting member from the first position to the second position, the cover member slides in the axial direction, while maintaining a constant radial distance from the hard member.

* * * * *